United States Patent

Nyfeler et al.

Patent Number: 4,705,800
Date of Patent: Nov. 10, 1987

[54] DIFLUORBENZODIOXYL CYANOPYRROLE MICROBICIDAL COMPOSITIONS

[75] Inventors: Robert Nyfeler, Basel; Josef Ehrenfreund, Allschwil, both of Switzerland

[73] Assignee: Ciba-Geigy Corporation, Ardsley, N.Y.

[21] Appl. No.: 874,193

[22] Filed: Jun. 13, 1986

[30] Foreign Application Priority Data

Jun. 21, 1985 [CH] Switzerland .................. 2649/85

[51] Int. Cl.$^4$ ................... C07D 317/46; A01N 43/30
[52] U.S. Cl. ...................................... 514/422; 549/464
[58] Field of Search ...................... 548/526; 514/422

[56] References Cited

U.S. PATENT DOCUMENTS 4,543,361 9/1985 Muchowski et al. .............. 514/422
4,548,951 10/1985 Muchowski et al. ........... 548/526 X

FOREIGN PATENT DOCUMENTS 2927480 1/1980 Fed. Rep. of Germany.

OTHER PUBLICATIONS van Leusen, et al.; Tetrahedron Letters, 52, (1972), pp. 5337–5340.
Muller; Angewandte Chemie, 61, pp. 178–183, (1949).

Primary Examiner—Joseph Paul Brust
Attorney, Agent, or Firm—Edward McC. Roberts; Meredith C. Findlay

[57] ABSTRACT

The invention relates to novel 3-phenyl-4-cyanopyrrole derivatives of the general formula

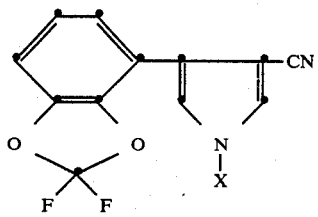

wherein X has the following meaning:

A: hydrogen or CO—$R_1$, wherein $R_1$ is $C_1$–$C_6$alkyl which is unsubstituted or substituted by halogen or $C_1$–$C_3$alkoxy; or is $C_3$–$C_6$alkenyl, $C_3$–$C_6$alkylnyl, or $C_1$–$C_6$alkoxy which is unsubstituted or substituted by halogen or $C_1$–$C_3$alkoxy; or is $C_3$14 $C_6$alkenyloxy, or $C_3$–$C_6$cycloalkyl;

B: S—$R_2$, wherein $R_2$ is $C_1$–$C_3$haloalkyl;

C: CH(Y)$R_3$, wherein $R_3$ is hydrogen or $C_1$–$C_8$haloalkyl and Y is hydroxy, halogen or OC(O)$R_4$, wherein $R_4$ is $C_1$–$C_8$alkyl, $C_1$–$C_8$haloalkyl, $C_2$–$C_6$alkenyl, or $C_1$–$C_6$alkoxycarbonyl; or D: CH$_2$—Z, wherein Z is the group

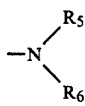

in which formula each of $R_5$ and $R_6$ independently of the other is hydrogen, $C_1$–$C_6$alkyl which is unsubstituted or substituted by cyano or $C_1$–$C_6$alkoxycarbonyl; or is $C_3$–$C_6$alkenyl, $C_3$–$C_6$alkynyl, $C_3$–$C_7$cycloalkyl, or phenyl which is unsubstituted or substituted by halogen, $C_1$–$C_6$alkyl, $C_1$–$C_6$haloalkyl or $C_1$–$C_6$alkoxy, with the proviso that only $R_5$ or $R_6$ may be hydrogen.

11 Claims, No Drawings

DIFLUORBENZODIOXYL CYANOPYRROLE MICROBICIDAL COMPOSITIONS

The present invention relates to novel substituted 3-phenyl-4-cyanopyrrole derivatives, to the preparation thereof and to microbicidal compositions which contain, as active ingredient, at least one of these compounds. The invention also relates to the preparation of said compositions and to the use of the novel compounds and compositions for controlling harmful microorganisms, in particular phytopathogenic fungi.

The compounds of this invention have the general formula I

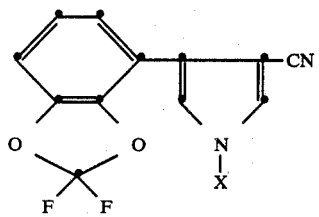
(I)

wherein X has the following meanings:

A: hydrogen or CO—$R_1$, wherein $R_1$ is $C_1$–$C_6$alkyl which is unsubstituted or substituted by halogen or $C_1$–$C_3$alkoxy; or is $C_3$–$C_6$-alkenyl, $C_3$–$C_6$alkynyl, or $C_1$–$C_6$alkoxy which is unsubstituted or substituted by halogen or $C_1$–$C_3$alkoxy; or is $C_3$–$C_6$alkenyloxy, $C_3$–$C_6$cycloalkyl or tetrahydrofur-2-yl;

B: S—$R_2$, wherein $R_2$ is $C_1$–$C_3$haloalkyl;

C: CH(Y)$R_3$, wherein $R_3$ is hydrogen or $C_1$–$C_8$haloalkyl and Y is hydroxy, halogen or OC(O)$R_4$, wherein $R_4$ is $C_1$–$C_8$alkyl, $C_1$–$C_8$haloalkyl, $C_2$–$C_6$alkenyl, tetrahydrofur-2-yl, tetrahydropyran-2-yl or $C_1$–$C_6$alkoxycarbonyl;

D: $CH_2$—Z, wherein Z is one of the groups

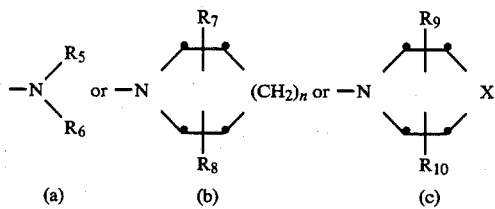

in which formulae each of $R_5$ and $R_6$ independently of the other is hydrogen, $C_1$–$C_6$alkyl which is unsubstituted or substituted by cyano or $C_1$–$C_6$alkoxycarbonyl; or is $C_3$–$C_6$alkenyl, $C_3$–$C_6$alkynyl, $C_3$–$C_7$cycloalkyl, or phenyl which is unsubstituted or substituted by halogen, $C_1$–$C_6$alkyl, $C_1$–$C_6$haloalkyl and/or $C_1$–$C_6$alkoxy, with the proviso that only $R_5$ or $R_6$ may be hydrogen; each of $R_7$ and $R_8$ independently of the other is hydrogen, $C_1$–$C_6$alkyl or $C_1$–$C_6$alkoxycarbonyl, or both together form a fused aromatic ring; each of $R_9$ and $R_{10}$ independently of the other is hydrogen, $C_1$–$C_6$alkyl or $C_1$–$C_6$alkoxycarbonyl; and X is oxygen, sulfur,

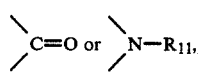

wherein $R_{11}$ is hydrogen, $C_1$–$C_6$alkyl, formyl, $C_1$–$C_6$alkanoyl or $C_1$–$C_6$alkoxycarbonyl; and n is 0 or 1.

Depending on the number of indicated carbon atoms, alkyl by itself or as moiety of another substituent will be understood as meaning for example the following groups: methyl, ethyl, propyl, butyl, pentyl, hexyl etc. and the isomers thereof, e.g. isopropyl, isobutyl, tert-butyl, isopentyl etc. Haloalkyl is a mono- to perhalogenated alkyl substituent, e.g. $CH_2Cl$, $CHCl_2$, $CCl_3$, $CH_2Br$, $CHBr_2$, $CBr_3$, $CH_2F$, $CHF_2$, $CF_3$, $CCl_2F$, $CCl_2$—$CHCl_2$, $CH_2CH_2F$, $CI_3$ etc. Throughout this specification, halogen will be understood as meaning fluorine, chlorine, bromine or iodine, with fluorine, chlorine or bromine being preferred. $C_3$–$C_6$Alkenyl is an unsaturated, aliphatic radical containing one or more double bonds, e.g. 1-propenyl, allyl, 1-butenyl, 2-butenyl, 3-butenyl, $CH_3CH$=$CHCH$=$CH$-etc. Alkynyl will be understood as meaning unsaturated, aliphatic radicals containing a maximum of 6 carbon atoms, e.g. propargyl, 2-butynyl, 3-butynyl etc.

Under normal conditions the compounds of formula I are stable oils, resins or mainly crystalline solids which are distinguished by extremely valuable microbicidal properties. They can be used for example in agriculture or related fields preventively or curatively for controlling phytopathogenic microorganisms. The compounds of formula I are distinguished by a very good fungicidal activity in wide ranges of concentrations and their use poses no problems.

Compounds of formula I which are preferred on account of their pronounced microbicidal properties are those containing as X the following substituents or combinations of these substituents: hydrogen or CO—$R_1$, wherein $R_1$ is $C_1$–$C_6$alkyl which is unsubstituted or substituted by halogen or $C_1$–$C_3$alkoxy; or is $C_3$–$C_6$alkenyl, $C_3$–$C_6$alkynyl, or $C_1$–$C_6$alkoxy which is unsubstituted or substituted by halogen or $C_1$–$C_3$alkoxy; or is $C_3$–$C_6$alkenyloxy, $C_3$–$C_6$cycloalkyl or tetrahydrofur-2-yl.

Among the compounds of formula I which carry combinations of substituents defined in the above group, those compounds are particularly preferred wherein X has the following meanings: hydrogen or CO—$R_1$, wherein $R_1$ is $C_1$–$C_4$alkyl which is unsubstituted or substituted by chlorine, bromine or $C_1$–$C_3$alkoxy; or is $C_3$–$C_4$alkenyl, $C_3$–$C_4$alkynyl, or $C_1$–$C_4$alkoxy which is unsubstituted or substituted by chlorine, bromine or $C_1$–$C_3$alkoxy; or is $C_3$–$C_4$alkenyloxy, $C_3$–$C_6$cycloalkyl or tetrahydrofur-2-yl.

Among the compounds of formula I, the following individual substances are preferred, in particular on account of their excellent fungicidal properties:

3-(2,2-difluorobenzodioxol-4-yl)-4-cyanopyrrole (comp. 1.1)

1-acetyl-3-(2,2-difluorobenzodioxol-4-yl)-4-cyanopyrrole (comp. 1.2)

1-methoxyacetyl-3-(2,2-difluorobenzodioxol-4-yl)-4-cyanopyrrole (comp. 1.15)

1-methoxycarbonyl-3-(2,2-difluorobenzodioxol-4-yl)-4-cyanopyrrole (comp. 1.24)

1-allyloxycarbonyl-3-(2,2-difluorobenzodioxol-4-yl)-4-cyanopyrrole (comp. 1.30)

1-n-propoxyacetyl-3-(2,2-difluorobenzodioxol-4-yl)-4-cyanopyrrole (comp. 1.32)

In addition, the first-named compound is particularly significant as an intermediate for the synthesis of further fungicidal substances.

In accordance with the present invention, the compounds of formula I are prepared (a) in alkaline medium by conducting a Michael cycloaddition reaction of the 2,3-(difluoromethylenedioxy)cinnamonitrile of formula II with p-toluenesulfonylmethyl isocyanide, with elimination of p-toluenesulfinic acid or of a salt thereof, in an organic solvent:

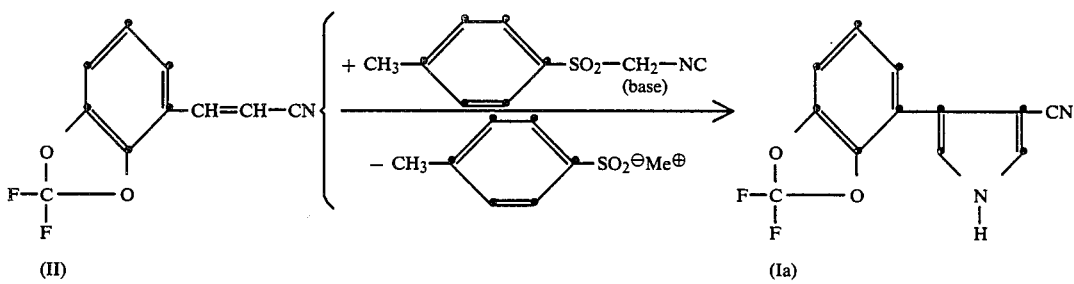

(II)           (Ia)

Me⊕ being an alkali metal ion or an alkaline earth metal ion, and (b) by subsequently acylating the compound of formula Ia with a compound of formula III, in the presence of an acid acceptor and optionally of a catalyst, in an organic solvent:

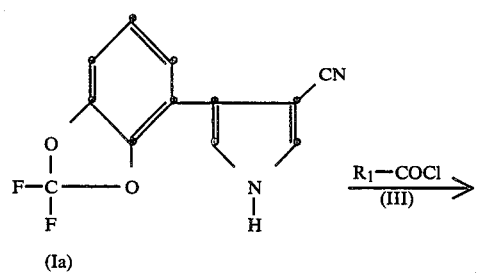

(Ia)

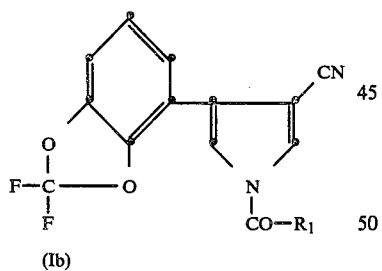

(Ib)

$R_1$ being as defined above for formula I, or (c) by sulfenylising the compound of formula Ia with a reactive acid derivative of a sulfenic acid of formula IV $$R_2S-OH \qquad (IV)$$

at the nitrogen atom of the pyrrole, in the presence of an acid acceptor, optionally in an organic solvent, $R_2$ being as defined above for formula I, or (d) by reacting the compound of formula Ia with an aldehyde of formula V $$R_3-CHO \qquad (V)$$

to give a hydroxy derivative of formula Ic

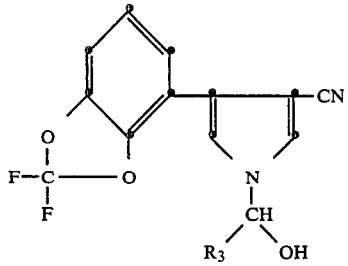

(Ic)

and converting said hydroxy derivative into another product of formula I by replacing the OH group by another radical Y, said replacement being effected by converting a compound of formula Ic either with an acid of formula VI $$R_4-COOH \qquad (VI)$$

or, preferably, with a reactive acid derivative thereof, most preferably an acid halide, e.g. an acid chloride or acid bromide, or with the acid anhydride thereof, into an acyloxy product of formula Id

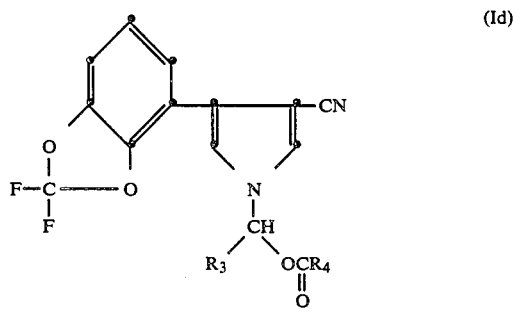

(Id)

or by first replacing the OH group in a compound of formula Ic by a halogen atom, preferably a chlorine or bromine atom, in conventional manner to give a compound of formula Ie

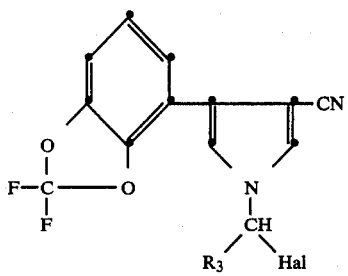

and then further converting said halogenated product by reaction with a salt of formula VII

into a compound of formula Id, the substituents in formulae Ic, Id, Ie, V, VI and VII being as defined for formula I, and Hal being halogen and $M^\oplus$ being a metal cation, preferably an alkaline earth metal cation or, most preferably, an alkai metal cation, e.g. $Ca^{\oplus\oplus}$, $Mg^{\oplus\oplus}$, $Na^\oplus$ or $K^\oplus$, or (e) either by reacting the compound of formula Ia with a compound of formula VIII

wherein Z is as defined above for formula I, and formaldehyde, in a protic solvent, in the temperature range from 0° to 120° C., preferably from 20° C. to reflux temperature, and in the presence of a basic catalyst; or by reacting the compound of formula Ia with a compound of formula VIII and 1,3,5-trioxane or paraformaldehyde, in an aprotic solvent, in the presence of a basic catalyst, and in the temperature range from 0° to 120° C., preferably from 20° to 80° C.

Reaction step (a):

Here the p-tolylsulfonyl group stands for a large number of groups which are able to activate the methylene group in the methyl isocyanide radical for a Michael addition reaction. Further preferred examples of such activating groups are benzenesulfonyl, p-chlorobenzenesulfonyl, lower alkylsulfonyl such as mesyl.

The cycloaddition is advantageously carried out in the presence of a non-nucleophilic base. Suitable bases are alkali metal hydrides such as sodium hydride, or alkali metal carbonates or alkaline earth metal carbonates such as $Na_2CO_3$, $K_2CO_3$, or alkali metal alcoholates such as $(CH_3)_3CO^\ominus K^\oplus$ and others. The base is advantageously used in at least equimolar amount, based on the starting materials.

It is convenient to conduct the cycloaddition reaction in an inert solvent. Examples of preferably anhydrous solvents suitable for the cycloaddition are: aromatic and aliphatic hydrocarbons such as benzene, toluene, xylenes, petroleum ethers, ligroin, cyclohexane; ethers and ethereal compounds such as dialkyl ethers (diethyl ether, diisopropyl ether, tert-butyl methyl ether etc.) dimethoxymethane, tetrahydrofuran, anisole; sulfones such as dimethyl sulfoxide; dimethylformamide; and mixtures of such solvents with one another.

The cycloaddition is normally carried out in the temperature range from −30° to +120° C., preferably from −30° to +50° C., or at the boiling point of the solvent of solvent mixture.

When choosing suitable bases, the cycloaddition can also conveniently be carried out in aqueous medium. Suitable bases in such cases are water-soluble inorganic and organic bases, in particular alkali metal hydroxides such as LiOH, NaOH or KOH, and ammonium bases, e.g. tetraalkylammonium hydroxides such as $(CH_3)_4NOH$. At least an equimolar amount of base is used, based on the starting materials. When using aqueous bases, it is advantageous to conduct the reaction in a heterogeneous two-phase system.

Examples of suitable solvents for the organic water-immiscible phase are: aliphatic and aromatic hydrocarbons such as pentane, hexane, cyclohexane, petroleum ether, ligroin, benzene, toluene, xylenes etc.; halogenated hydrocarbons such as dichloromethane, chloroform, carbon tetrachloride, ethylene dichloride, 1,2-dichloroethane, tetrachloroethylene etc; or aliphatic ethers such as diethyl ether, disopropyl ether, tert-butylmethyl ether etc.

The presence of a phase tranfer catalyst can be of advantage in this mode of carrying out the reaction in order to hasten the rate of reaction. Examples of such catalysts are: tetraalkylammonium halides, hydrogen sulfates or hydroxides such as tetrabutylammonium chloride, bromide or iodide; triethylbenzylammonium chloride or bromide; tetrapropylammonium chloride, bromide or iodide etc. Phosphonium salts are also suitable for use as phase transfer catalysts.

The phase transfer catalysed cycloaddition can be carried out in the temperature range from 0° to 80° C., preferably from 10° to 50° C. or at the boiling point of the solvent mixture. The cycloaddition can be carried out in the described embodiment of the process under normal pressure. The reaction time is in general from 1 to 16 hours, and in phase transfer catalysis from ½ hour to 10 hours.

Reaction step (b):

The acylation of the compound of formula Ia is carried out under the normal conditions known to the person skilled in the art.

Examples of suitable inert solvents or diluents are: aliphatic and aromatic hydrocarbons such as benzene, toluene, xylenes, petroleum ether; halogenated hydrocarbons such as chlorobenzene, methylene chloride, ethylene chloride, chloroform, carbon tetrachloride, tetrachloroethylene; ethers and ethereal compounds such as dialkyl ethers (diethyl ether, diisopropyl ether, tert-butylmethyl ether etc.), dioxane, tetrahydrofuran; nitriles such as acetonitrile, propionitrile; ketones such as acetone, diethyl ketone, methyl ethyl ketone; and mixtures of such solvents with each other. Dimethylformamide, tetrahydrofuran and dioxane are preferred.

Examples of suitable acid acceptors are inorganic bases, e.g. oxides, hydroxides, carbonates or bicarbonates of alkali metals or alkaline earth metals, as well as alkali metal hydrides or alkali metal acetates, and also organic bases, e.g. tertiary amines such as trialkylamines (trimethylamine, triethylamine etc.), pyridine or pyridine bases (4-dimethylaminopyridine, 4-pyrrolidylaminopyridine). Preferred acid acceptors are trialkylamines such as trimethylamine or triethylamine.

The reaction temperature is variable depending on the reaction conditions. It is generally in the range from −25° to +100° C., preferably from −10° to +75° C.

Reaction step (c):

Suitable reactive sulfenic acid derivatives for this sulfenylation reaction are e.g. the lower alkyl esters and, preferably, the sulfenic acid halides, in particular the chlorides and bromides, with the chlorides being especially preferred. Lower alkyl will here be understood as meaning $C_1$–$C_6$alkyl.

Both organic and inorganic bases may be successfully employed in the above reaction. Examples of suitable inorganic bases are alkali metal carbonates and alkaline earth metal carbonates such as sodium carbonate, potassium carbonate, calcium carbonate etc. Examples of suitable organic bases are tertiary amines such as trialkylamines (triethylamine, methyldiethylamine), N,N-dimethoxycyclohexylamine, N-methylpiperidine, N,N-dimethylaniline or pyridines. Trialkylamines are preferred. It is advantageous to use the base in stoichiometric amount or in excess thereof, e.g. in up to 100% excess of the stoichiometric amount, based on the pyrrole of formula Ia. The reactive derivative of the sulfenic acid of formula IV is also used in stoichiometric amount or in excess thereof.

The sulfenylation reaction may be carried out in the presence or absence, preferably in the presence, of an inert solvent or mixture of solvents. In principle, the customary organic solvents are suitable for this reaction, provided they contain no reactive hydrogen atoms. Examples of suitable solvents are: aliphatic and aromatic hydrocarbons such as benzene, toluene, xylenes, petroleum ethers; halogenated hydrocarbons such as chlorobenzene, methylene chloride, ethylene chloride, chloroform, carbon tetrachloride, tetrachloroethylene; ethers and ethereal compounds such as dialkyl ethers (diethyl ether, diisopropyl ether, tert-butylmethyl ether etc.), ethylene glycol di- and monoether and diethylene glycol di- and monoether, containing 1 to 4 carbon atoms in each of the alkyl moieties, for example ethylene glycol dimethyl, diethyl and di-n-butyl ether, diethylene glycol diethyl and di-n-butyl ether, ethylene glycol monoethyl ether and diethylene glycol monomethyl ether; furan, dimethoxyethane, dioxane, tetrahydrofuran, anisole; sulfones such as dimethyl sulfoxide; ketones such as acetone, methyl ethyl ketone; esters such as ethyl acetate, propyl acetate, butyl acetate; and mixtures of such solvents with one another. In some cases the sulfenylating reagent of the formula IV may itself act as solvent.

To hasten the reaction rate, a catalyst such as 4-dimethylaminopyridine may be added, if appropriate.

The sulfenylation reaction is normally carried out in the temperature range from −30° to +100° C., preferably from −10° to +20° C. The reaction time is then generally from about ½ hour to 20 hours. However, addition of a reaction catalyst can reduce the reaction time to less than ½ hour.

Reaction step (d):

The reaction of the compound of formula Ia with aldehydes of formula V can be carried out in the presence or absence of an inert solvent or mixture of solvents. Examples of suitable solvents are: aromatic hydrocarbons such as benzene, toluene or xylenes; halogenated hydrocarbons such as chlorobenzene; aliphatic hydrocarbons such as petroleum ether; ether and ethereal compounds such as dialkyl ethers (diethyl ether, diisopropyl ether, tert-butylmethyl ether etc.), furan, dimethoxyethane, dioxane, tetrahydrofuran; and dimethylformamide etc.

The reaction of compounds of formula Ia with compounds of formula V is conveniently carried out without a solvent but using an excess of the aldehyde of formula V. Depending on the nature of the aldehyde, the reaction is carried out in solution or in the melt. The reaction rate can be speeded up by adding an acid or basic catalyst. Examples of suitable acid catalysts are non-aqueous hydrogen halides and mineral acids such as HCl, HBr or $H_2SO_4$, and also concentrated hydrochloric acid. Examples of suitable basic catalysts which can be used are: trialkylamines (trimethylamine, triethylamine, dimethylethylamine etc.), alkali metal carbonates and alkaline earth metal carbonates (such as $Na_2CO_3$, $BaCO_3$, $MgCO_3$, $K_2CO_3$ etc.), or alkali metal alcoholates (such as $NaOCH_3$, $NaOC_2H_5$, $KO(iso-C_3H_7)$, $KO(tert-butyl)$). The reaction temperatures are normally in the range from 0° to 200° C., preferably from 0° to 160° C., and the reaction time is from 1 to 24 hours, preferably from 1 to 4 hours.

The reaction to replace the free hydroxyl group in the compounds of formula Ic by a group Y is preferably carried out in an inert solvent. Examples of such solvents are: aromatic and aliphatic hydrocarbons such as benzene, toluene, xylenes, petroleum ether, ligroin or cyclohexane; halogenated hydrocarbons such as chlorobenzene, methylene chloride, ethylene chloride, chloroform, carbon tetrachloride or tetrachloroethylene; ethers and ethereal compounds such as diethyl ether, diisopropyl ether, tert-butylmethyl ether, dimethoxyethane, dioxane, tetrahydrofuran or anisole; esters such as ethyl acetate, propyl acetate or butyl acetate; nitriles such as acetonitrile; or compounds such as dimethyl sulfoxide, dimethylformamide, and mixtures of such solvents with one another.

The introduction of the group Y is effected by conventional methods. If Y is chlorine, the reagent employed is e.g. phosphoroxy chloride, phosphorus trichloride, phosphorous pentachloride or, preferably, thionyl chloride. The reaction is normally carried out in the temperature range from 0° to 120° C. If Y is bromine, the preferred reagent is phosphorus tribromide or phosphorus pentabromide and the reaction is carried out in the temperature range from 0° to 50° C. If Y is the —O—C(O)—$R_4$ group, the reagent employed will normally be the corresponding acid halide, preferably acid chloride. In this case it is convenient to carry out the reaction in the temperature range from −20° to +50° C., preferably from −10° to +30° C., and in the presence of a weak base such as pyridine or triethylamine. To speed up the reaction it is also possible to add a 4-dialkylaminopyridine such as 4-dimethyl- or 4-diethylaminopyridine as catalyst.

The reaction of compounds of formula Ie with salts of formula VII is usually carried out in the presence of a commonly employed inert solvent or mixture of solvents. Examples of such solvents are: aromatic and aliphatic hydrocarbons such as benzene, toluene, xylenes, petroleum ether, ligroin or cyclohexane; ethers and ethereal compounds such as dialkyl ethers, e.g. diethyl ether, diisopropyl ether, tert-butylmethyl ether, dimethoxyethane, dioxane, tetrahydrofuran or anisole; esters such as ethyl acetate, propyl acetate or butyl acetate; nitriles such as acetonitrile; or compounds such as dimethyl sulfoxide, dimethylformamide and mixtures of such solvents with one another.

The course of this reaction can be advantageously influenced by addition of catalytic amounts of a crown ether, e.g. 18-crown-6 or 15-crown-5. The reaction temperature is generally in the range from 0° to 150° C., preferably from 20° to 80° C. The reaction time is from 1 to 24 hours.

In a preferred embodiment, the preparation of compounds of formula Id, in particular those in which R₃ is CCl₃ or R₃ is H, starting from compounds of formula Ia, is effected by carrying out the reaction continuously without isolation of the intermediate formed. This reaction is conveniently carried out in one of the solvents or diluents referred to above, most suitably in e.g. an ethereal compound such as tetrahydrofuran, and in the presence of a weak base such as a trialkylamine (triethylamine) or pyridine. Chloral or paraformaldehyde is used as reagent. The reaction can be speeded up by adding a catalyst such as 1,8-diazabicyclo[5.4.0]undec-7-ene [DBU]. The temperature in this first reaction step is in the range from −20° to +100° C., preferably from 0° to +50° C., and the reaction time is from ½ hour to 2 hours. A hydroxy derivative of formula Ic is obtained as intermediate. This intermediate is not isolated, but is reacted with a compound of formula VI, in the same reaction solution, in the temperature range from −30° to +30° C., preferably from −10° to 0° C., and in the presence of catalytic amounts of a 4-dialkylaminopyridine, preferably 4-dimethylaminopyridine. The reaction time of this second step is from ½ hour to 16 hours.

The starting materials of formulae V, VI and VII are generally known or they can be prepared by methods which are known per se.

Reaction step (e):

The reaction of the compound of formula Ia with a compound of formula VIII is preferably carried out in a suitable inert solvent. Examples of suitable protic solvents are: water, alcohols (preferably alkanols such as methanol, ethanol, isopropanol, n-propanol etc.), or carboxylic acids (preferably alkanecarboxylic acids such as formic acid, acetic acid, propionic acid etc.). If the process is carried out in a protic solvent, then the following reaction catalysts can, for example, be used: organic bases such as 1,8-diazabicyclo[5.4.0]undec-7-ene, tertiary amines such as trialkylamines (trimethylamine, triethylamine, dimethylethylamine etc.), triethylenediamine, piperidine, pyridine, 4-dimethylaminopyridine, 4-pyrrolidylpyridine etc., or inorganic bases such as the oxides, hydroxides, hydrides, carbonates, bicarbonates and alcoholates of alkali metals or alkaline earth metals (e.g. Na₂CO₃, BaCO₃, MgCO₃, K₂CO₃, NaHCO₃, KHCO₃, Ca(HCO₃)₂, NaOCH₃, NaOC₂H₅, KO(iso-C₃H₇), KO(tert-butyl), NaH, CaO etc.); organic acids such as carboxylic acids (acetic acid, formic acid, propionic acid etc.), aliphatic and aromatic sulfonic acids such as methanesulfonic acid, ethanesulfonic acid, toluenesulfonic acid, benzenesulfonic acid etc.; inorganic acids such as mineral acids, e.g. phosphoric acid, sulfuric acid, nitric acid or hydrohalic acids (hydrochloric acid, hydrobromic acid, hydriodic acid or hydrofluoric acid). It is convenient to use catalytic amounts of acids or bases in this variant. In general, an excess of amine of formula VIII will suffice. In this variant the formaldehyde is preferably used in the form of its aqueous solution (formaline) or as trimer (1,3,5-trioxane) or polymer (paraformaldehyde).

Suitable aprotic solvents are e.g.: aliphatic or aromatic hydrocarbons such as benzene, toluene, xylenes, petroleum ether, ligroin or cyclohexane; ethers and ethereal compounds such as diethyl ether, diisopropyl ether, tert-butylmethyl ether, dimethoxyethane, tetrahydrofuran, dioxane or anisole; esters such as ethyl acetate, propyl acetate or butyl acetate, or compounds such as dimethylformamide, dimethyl sulfoxide, or mixtures of such solvents with one another. The catalysts employed are e.g. the bases referred to above. In this reaction step it is preferred to use the formaldehyde in the form of 1,3,5-trioxane or paraformaldehyde.

The sulfenic acids of formula IV and the amines of formula VIII are known or they can be prepared by methods known per se.

The cinnamonitrile of formula II as starting material for the compound of formula Ia is prepared from the 2,3-(difluoromethylenedioxy)aniline of formula IX which is converted into the diazonium salt of formula X in the conventional manner known to the skilled person:

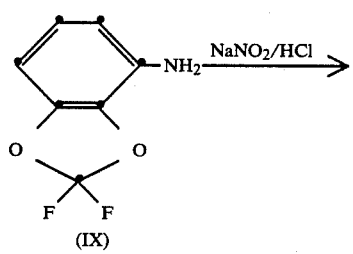

(IX)

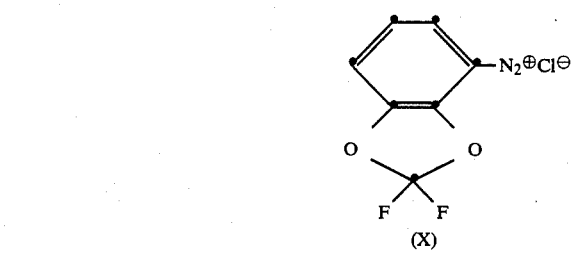

(X)

The diazonium salt of formula X is then allowed to react with the acrylonitrile of formula XI, in the presence of Cu(I) chloride in an aqueous reaction medium containing a dialkyl ketone as a solubiliser, to give the adduct of formula XII

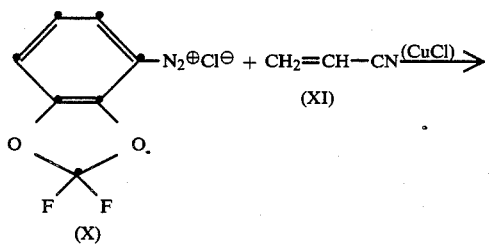

(X)    (XI)

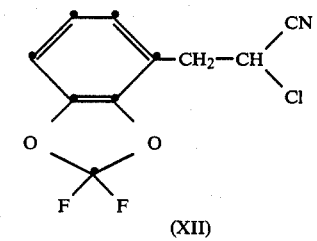

(XII)

Subsequently, HCl is eliminated by reacting the compound of formula XII with an acid acceptor in an inert organic solvent, thus affording the 2,3-(difluoromethylenedioxy)cinnamonitrile of formula II, which product is a mixture of cis and trans isomers which can be resolved by chromatography in conventional manner:

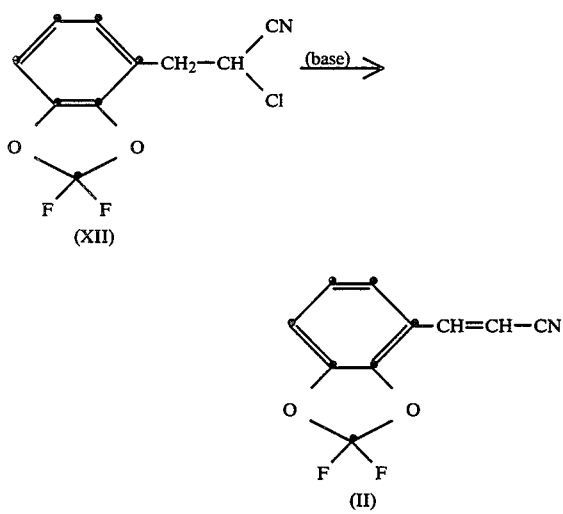

The reaction of the diazonium salt of formula X with the acrylonitrile of formula XI is a modification of the normal Sandmeyer method under the conditions of the Meerwein reaction of aromatic diazonium compounds with α-,β-unsaturated carbonyl compounds, whereby the replacement of the diazonium group by halogen is restrained in favour of the addition reaction (q.v. E. Müller, Angewandte Chemie 61, pp. 178–183, 1949).

In the practical performance of the reaction, the reactants (diazonium salt and acrylonitrile) are employed in a ratio in the range from 1:1 to 1:8, preferably in a ratio of 1:2. The reaction temperatures are in the range from 20° to 50° C., preferably from 25° to 35° C. The reaction time is from ½ hour to 10 hours, preferably from 1 to 3 hours. It is preferred to use ethyl methyl ketone as solubiliser in the aqueous reaction medium.

Inert solvents for the reaction to eliminate HCl from the compound of formula XII are for example aliphatic and aromatic hydrocarbons such as benzene, toluene, xylenes, petroleum ether; halogenated hydrocarbons such as chlorobenzene, methylene chloride, ethylene chloride, chloroform, carbon tetrachloride, tetrachloroethylene; ether and etheral compounds such as dialkyl ethers (diethyl ether, diisopropyl ether, tert-butylmethyl ether etc.), dioxane, tetrahydrofuran; nitriles such as acetonitrile, propionitrile; N,N-dialkylated amides such as dimethylformamide; dimethyl sulfoxide; ketones such as acetone, diethyl ketone, methyl ethyl ketone, and mixtures of such solvents with one another. Suitable acid acceptors are weakly nucleophilic organic bases, preferably trialkylamines. The elimination reaction is carried out in the temperature range from room temperature to the reflux temperature of the solvent employed, preferably in the range from 30° to 60° C. The reaction time is from 1 to 24 hours, preferably from 3 to 12 hours.

The compound of formula II is a valuable intermediate for the preparation of fungicides and, as novel compound, constitutes an object of the present invention.

Some 3-phenyl-4-cyanopyrrole derivatives are known as fungicides. Such compounds are described e.g. in Tetrahedron Letters 52, pp. 5337–5340 (1972) and in German Offenlegungsschrift No. 29 27 480. However, the effectiveness of the known derivatives has not always proved to be entirely satisfactory to the desired degree.

Surprisingly, it has been found that the compounds of formula I of this invention have, for practical field application purposes, a very advantageous pesticidal activity spectrum against harmful microorganisms, in particular against phytopathogenic fungi and bacteria. Compounds of formula I have very advantageous curative, systemic and, in particular, preventive propperties, and can be used for protecting numerous cultivated plants. With the compounds of formula I it is possible to inhibit or destroy the pests which occur in plants or in parts of plants (fruit, blossoms, leaves, stems, tubers, roots) in different crops of userful plants, while at the same time the parts of plants which grow later are also protected from attack by phytopathogenic microorganisms.

The compounds of formula I are effective for example against the phytopathogenic fungi belonging to the following classes: Ascomycetes, e.g. Erysiphe, Sclerotinia, Fusarium, Monilinia, Helminthosporium; Basidiomycetes, e.g. Puccinia, Tilletia, Rhizoctonia; as well as the Oomycetes belonging to the class of Phycomycetes, e.g. Phytophthora. As plant protective agents, the compounds of formula I can be used with particular success against important noxious fungi of the *Fungi imperfecti* family, e.g. against Cercospora, Pyricularia and, in particular, against Botrytis. Botrytis spp. (*B. cinerea, B. allii*) and the grey mould on vines, strawberries, apples, onions and other varieties of fruit and vegetables are a source of considerable economic damage. In particular compound 1.1 of Table 1 has a wide activity spectrum. It exhibits an excellent fungicidal activity not only against Pyricularia, Botrytis and Rhizoctonia but is also suitable for successfully controlling Erysiphe and Venturia species. Furthermore, the compounds of formula I have a systemic action. In addition, compounds of formula I can be successfully used for protecting perishable goods of vegetable or animal origin. They control mould fungi such as Penicillium, Aspergillus, Rhizopus, Fusarium, Helminthosporium, Nigrospora and Alternaria, as well as bacteria such as butyric acid bacteria and yeast fungi such as Candida. Furthermore, these compounds have excellent activity against fungi which occur in seeds or in the soil. As plant protective agents, the compounds of formula I have a very advantageous activity spectrum for practical application in agriculture for protecting cultivated plants, without damaging said plants by harmful side-effects.

The compounds of formula I can also be used as dressing agents for protecting seeds (fruit, tubers, grains) and plant cuttings against fungus infections and against phytopathogenic fungi which occur in the soil. The compounds of formula I are in particular very effective tive cereal dressing agents for controlling fungus organisms such as Fusarium, Helminthosporium and Tilletia species.

Accordingly, the invention also relates to microbicidal compositions and to the use of the compounds of formula I for controlling phytopathogenic microoganisms, in particular phytopathogenic fungi, and for the preventive treatment of plants and stored goods of vegetable or animal origin to protect them from attack by such microorganisms.

Target crops to be protected within the scope of the present invention comprise e.g. the following species of plants: cereals (wheat, barley, rye, oats, rice, sorghum and related crops), beet (sugar beet and fodder beet), pomes, drupes and soft fruit (apples, pears, plums, peaches, almonds, cherries, strawberries, rasberries and blackberries), leguminous plants (beans, lentils, peas, soybeans), oil plants (rape, mustard, poppy, olives, sunflowers, coconut, castor oil plants, cocoa beans, groundnuts), cucumber plants (cucumber, marrows, melons), fibre plants (cotton, flax, hemp, jute), citrus fruit (oranges, lemons, grapefruit, mandarins), vegetables (spinach, lettuce, asparagus, cabbages, carrots, onions, tomatoes, potatoes, paprika), lauraceae (avocados, cinnamon, camphor), or plants such as maize, tobacco, nuts, coffee, sugar cane, tea, vines, hops, bananas and natural rubber plants, as well as ornamentals (composites).

For storage protection, the compounds of formula I are used in unmodified form or, preferably, together with the adjuvants conventionally employed in the art of formulation, and are therefore formulated in known manner to e.g. emulsifiable concentrates, brushable pastes, directly sprayable or dilutable solutions, dilute emulsions, wettable powders, soluble powders, dusts, granulates and also encapsulations in e.g. polymer substances. The methods of application, such as spraying, atomising, dusting, scattering, coating or pouring, the formulation of the composition, are chosen in accordance with the intended objectives and the prevailing circumstances. Suitable rates of application are in general in the range from 0.01 to not more than 2 kg of active ingredient per 100 kg of substrate to be protected. However, they depend very materially on the nature (surface area, consistency, moisture content) of the substrate and its environmental influences.

Within the scope of this invention, storable goods will be understood as meaning natural substances of vegetable and/or animal origin and the products obtained therefrom by further processing, for example the plants listed below whose natural life cycle has been interrupted and the parts thereof (stalks, leaves, tubers, seeds, fruit, grains) which are in freshly harvested or further processed form (predried, moistened, crushed, ground, roasted). The following produce may be cited by way of example, without any restriction to the field of use within the scope of this invention: cereals (wheat, barley, rye, oats, rice, sorghum and related crops); beet (carrots, sugar beet and fodder beet); pomes, drupes and soft fruit (apples, pears, plums, peaches, almonds, cherries, strawberries, rasberries and blackberries); leguminous plants (beans, lentils, peas, soybeans); oil plants (rape, mustard, poppy, olives, sunflowers, coconuts, castor oil plants, cocoa beans, groundnuts); cucmber plants (cucumber, marrows, melons); fibre plants (cotton, flax, hemp, jute, ramie); citrus fruit; vegetables (spinach, lettuce, asparagus, cabbages, onions, tomatoes, potatoes, paprika); lauraceae (avocados, cinnamon, camphor), or maize, tobacco, nuts, coffee, sugar cane, tea, vines, chestnuts, hops, bananas, grass and hay.

Examples of natural products of animal origin are, in particular dried meat and processed fish products such as dry-cured meat, dry-cured fish, meat extracts, bone meal, fish meal and animal dry feeds.

The storable goods treated with compounds of formula I are given lasting protection from attack by mould fungi and other undesired microorganisms. The formation of toxic and in some cases carcinogenic mould fungi (aflatoxins and ochratoxins) is inhibited, the goods are preserved from deterioration, and their quality is maintained over a prolonged period of time. The method of the invention can be applied to all forms of dry and moist storable goods which are susceptible to attack by microorganisms such as yeast fungi, bacteria and, in particular, mould fungi.

A preferred method of applying the active ingredient comprises spraying or wetting the substrate with a liquid formulation, or mixing the substrate with a solid formulation, of the active ingredient. The invention also relates to the described method of preserving storable goods.

The compounds of formula I are normally applied in the form of compositions and can be applied to the crop area, plant or substrate to be treated, simultaneously or in succession, with further compounds. These compounds can be both fertilisers or micronutrient donors or other preparations that influence plant growth. They can also be selective herbicides, insecticides, fungicides, bactericides, nematicides, mollusicides or mixtures of several of these preparations, if desired together with further carriers, surfactants or application promoting adjuvants customarily employed in the art of formulation.

Suitable carriers and adjuvants can be solid or liquid and correspond to the substances ordinarily employed in formulation technology, e.g. natural or regenerated mineral substances, solvents, dispersants, wetting agents, tackifiers, thickeners, binders or fertilisers. Phospholipids are particularly advantageous adjuvants.

A preferred method of applying a compound of the formula I, or an (agro)chemical composition which contains at least one of said compounds, is foliar application. The number of applications and the rate of application depend on the risk of infestation by the corresponding pathogen (species of fungus). However, the compound of formula I can also penetrate the plant through the roots via the soil (systemic action) by impregnating the locus of the plant with a liquid formulation, or by applying the compounds in solid form to the soils, e.g. in granular form (soil application). The compounds of formula I may also be applied to seeds (coating) by impregnating the seeds either with a liquid formulation containing a compound of formula I, or coating them with a solid formulation. In special cases, further types of application are also possible, e.g. selective treatment of the plant stems or buds.

The compounds of formula I are used in unmodified form or, preferably, together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering, coating or pouring, are chosen in accordance with the intended objectives and the prevailing circumstances. Advantageous rates of application are normally from 50 g to 5 kg of active ingredient (a.i.) per hectare, preferably from 100 g to 2 kg a.i./ha, most preferably from 200 g to 600 g a.i./ha. The formulations, i.e. the compositions, preparations or mixtures containing the compound (active ingredient) of formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g.

xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils such as epoxidised coconut oil, sunflower oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly disposed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues, e.g. cork powder or sawdust.

Depending on the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylsulfonates.

The fatty sulfonates or sulfates are usually in the form of alkali metal salts, alkaline earth metal salts or unsubstituted or substituted ammonium salts and containing a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, caster oil polyglycol ethers, polypropylene/polyethylene oxide adducts, tributylphenoxypolyethyleneethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted of halogenated alkyl, benzyl or hydroxy-lower alkyl radicals. The salts are preferably in the form of halides, methylsulfates or ethylsulfates, e.g. stearyltrimethylammonium chloride or benzyldi(2-chloroethyl)ethylammonium bromide. In the field of storage protection, the auxiliaries which are acceptable for human and amimal nutrition are preferred.

The agrochemical compositions usually contain 0.1 to 99% by weight, preferably 0.1 to 95% by weight, of a compound of formula I, 99.9 to 1% by weight, preferably 99.8 to 5% by weight, of a solid or liquid adjuvant, and 0 to 25% by weight, preferably 0.1 to 25% by weight, of a surfactant.

Whereas commercial products will preferably be formulated as concentrates, the end user will normally employ dilute formulations.

The compositions may also contain further auxiliaries such as stabilisers, antifoams, viscosity regulators, binders, tackifiers as well as fertilisers or other active ingredients for obtaining special effects.

Such (agro)chemical compositions constitute an object of the present invention.

The invention is illustrated by the following non-limitative Examples (percentages and parts are by weight).

PREPARATORY EXAMPLES 1.1 Preparation of 2,3-(difluoromethylenedioxy)cinnamonitrile

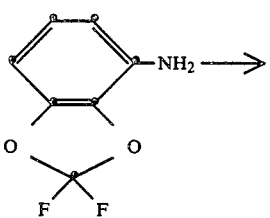

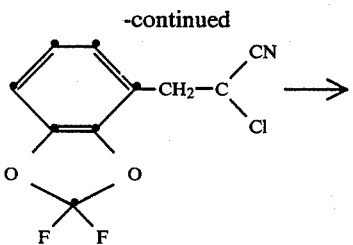

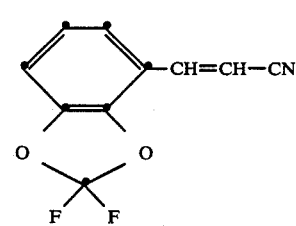

(a) 50 ml of 32% hydrochloric acid and 6 ml of water are added to a solution of 34.6 g of 4-amino-2,2-difluorobenzodioxole in 71 ml of acetic acid. A solution of 15 g of sodium nitrite in 30 ml of water is added dropwise at 0° C. to the resultant mixture. The batch is then stirred for 1 hour at 0° C. The resultant suspension is then run in portions at 27°-30° C. into 27 ml of acrylonitrile and 24 ml of ethyl methyl ketone. Simultaneously, a solution of 0.75 g of Cu(I) chloride in 7.5 ml of 32% hydrochloric acid is added dropwise from a separate drip funnel. When the dropwise addition is complete, the mixture is stirred for a further 30 minutes at 35° C. and then poured onto ice. The mixture is extracted twice with methylene chloride, the organic phases are extracted twice with dilute ice-cold sodium hydroxide solution, dried over sodium sulfate and filtered, and the filtrate is concentrated to a volume of 700 ml.

(b) 34.6 ml of triethylamine are added to the above methylene chloride solution, and the batch is heated under reflux for 12 hours. After cooling, the dark solution is poured into ice water. The phases are separated and the aqueous phase is extracted again with methylene chloride. The organic phases are extracted twice with ice-cold dilute hydrochloric acid and subsequently washed with a semi-saturated solution of sodium chloride, dried over sodium sulfate and filtered, and the filtrate is concentrated. By chromatography of the crude mixture of cis and trans isomers (eluant: a 20:1 mixture of petroleum distillate and ethyl acetate), the trans isomer (the main isomer in the mixture) of the above cinnamonitrile can be obtained in pure form. Yellowish crystals with a melting point of 53°-56°.

NMR (60 MHz, CFCl$_3$) 6.2 ppm (d, J=17 Hz, 1H); 7.2 ppm (s, 3H); 7.4 ppm (d, J=17 Hz, 1H).

1.2 Preparation of 3-(2,2-difluorobenzodioxol-4-yl)-4-cyanopyrrole

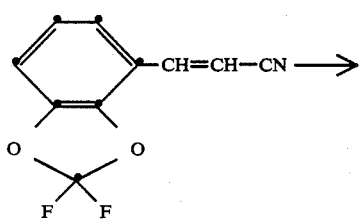

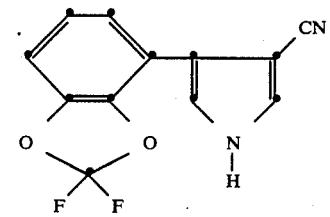

A solution of 38.8 g of the above cinnamonitrile and 43.4 g of p-toluenesulfonylmethyl isocyanide (tosmic) in 250 ml of tetrahydrofuran and a solution of 29.2 g of potassium tert-butylate in 250 ml of tetrahydrofuran are each added dropwise at −5° to +5° C. from two drip funnels to 100 ml of tetrahydrofuran. The mixture is then stirred for 1 hour at 0° C. and for a further 2 hours at room temperature. The reaction mixture is then poured into ice water and extracted twice with ethyl acetate. The organic extracts are washed four times with a semi-saturated solution of sodium chloride, dried over sodium sulfate, stirred with silica gel, a small amount of activated carbon and kieselguhr (Celite ®) and filtered, and the filtrate is concentrated. The residue is crystallised from a small amount of methylene chloride at −30° C., affording 16.5 g of beige crystals with a melting point of 197°-199° C.

1.3. Preparation of 1-acetyl-3-(2,2-difluorobenzodioxol-4-yl)-4-cyanopyrrole

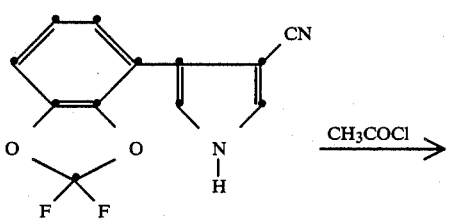

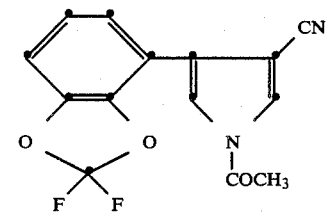

0.2 g of 4-dimethylaminopyridine and 1.6 ml of triethylamine are added to a solution of 2.5 g of the above pyrrole in 10 ml of tetrahydrofuran. A solution of 0.85 ml of acetyl chloride in 5 ml of tetrahydrofuran is then slowly added dropwise at −10° C. The reaction mixture is stirred for 16 hours in a thawing ice bath and then filtered, and the filtrate is concentrated. The solid residue is recrystallised from a mixture of toluene and petroleum distillate, affording crystalline N-(acetyl)-3-[2,2-difluorobenzodioxol-4-yl]-4-cyanopyrrole with a melting point of 133°-135° C.

Compounds 1.3 to 1.32 listed in the Table are prepared in analogous manner.

TABLE 1

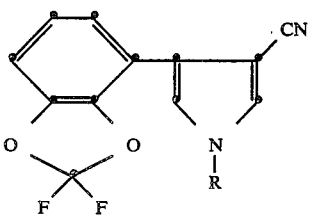

| Comp. | R | Chemicophysical data |
|---|---|---|
| 1.1 | H | m.p. 197–199° C. |
| 1.2 | —COCH$_3$ | m.p. 133–135° C. |
| 1.3 | —COCH$_2$CH$_3$ | m.p. 148–150° C. |
| 1.4 | —CO—C$_3$H$_7$(n) | m.p. 133–135° C. |
| 1.5 | —CO—C$_3$H$_7$(c) | |
| 1.6 | —CO—C$_4$H$_9$(n) | m.p. 122–125° C. |
| 1.7 | —CO—C$_4$H$_9$(s) | |
| 1.8 | —CO—C$_4$H$_9$(i) | |
| 1.9 | —CO—C$_4$H$_9$(t) | m.p. 141–143° C. |
| 1.10 | —CO—C$_5$H$_4$(n) | |
| 1.11 | —CO—C$_6$H$_{13}$(n) | |
| 1.12 | —CO—CH$_2$Cl | |
| 1.13 | —CO—CH$_2$Br | |
| 1.14 | —CO—CF$_3$ | |
| 1.15 | —CO—CH$_2$OCH$_3$ | m.p. 139–141° C. |
| 1.16 | —COCH$_2$CH$_2$OCH$_3$ | |
| 1.17 | —CO—CH=CH$_2$ | |
| 1.18 | —CO—CH=CH—CH$_3$ | m.p. 172–174° C. |
| 1.19 | —CO—C≡CH | |
| 1.20 | —CO—cyclopropyl | m.p. 195–197° C. |
| 1.21 | —CO—cyclopentyl | |
| 1.22 | —CO—cyclohexyl | |
| 1.23 | —CO—tetrahydrofur-2-yl | m.p. 116–118° C. |
| 1.24 | —CO—OCH$_3$ | m.p. 143–145° C. |
| 1.25 | —CO—OCH$_2$CH$_3$ | |
| 1.26 | —CO—OC$_4$H$_9$(n) | |
| 1.27 | —CO—OCH$_2$CH(CH$_3$)$_2$ | |
| 1.28 | —CO—OCH$_2$CH$_2$OCH$_3$ | |
| 1.29 | —CO—OCH$_2$CH$_2$Cl | |
| 1.30 | —CO—OCH$_2$CH=CH$_2$ | m.p. 126–128° C. |
| 1.31 | —COOCH$_{22}$CH$_2$Br | |
| 1.32 | —CO—CH$_2$—OCH$_2$CH$_2$CH$_3$ | |

2. Formulation Examples for liquid active ingredients of formula I (throughout, percentages are by weight)

| 2.1. Emulsifiable concentrates | (a) | (b) | (c) |
|---|---|---|---|
| a compound of Table 1 | 25% | 40% | 50% |
| calcium dodecylbenzenesulfonate | 5% | 8% | 6% |
| castor oil polyethylene glycol ether (36 moles of ethylene oxide) | 5% | — | — |
| tributylphenol polyethylene glycol ether (30 moles of ethylene oxide) | — | 12% | 4% |
| cyclohexanone | — | 15% | 20% |
| xylene mixture | 65% | 25% | 20% |

Emulsions of any required concentration can be produced from such concentrates by dilution with water.

| 2.2. Solutions | (a) | (b) | (c) | (d) |
|---|---|---|---|---|
| a compound of Table 1 | 80% | 10% | 5% | 95% |
| ethylene glycol monomethyl ether | 20% | — | — | — |
| polyethylene glycol (mol. wt. 400) | — | 70% | — | — |
| N—methyl-2-pyrrolidone | — | 20% | — | — |
| epoxidised coconut oil | — | — | 1% | 5% |
| petroleum distillate (boiling range 160–190° C.) | — | — | 94% | — |

These solutions are suitable for application in the form of microdrops.

| 2.3. Granulates | (a) | (b) |
|---|---|---|
| a compound of Table 1 | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| 2.4. Dusts | (a) | (b) |
|---|---|---|
| a compound of Table 1 | 2% | 5% |
| highly dispersed silicic acid | 1% | 5% |
| talcum | 97% | — |
| kaolin | — | 90% |

Ready-for-use dusts are obtained by intimately mixing the carriers with the active ingredient.

| 2.5. Wettable powders | (a) | (b) | (c) |
|---|---|---|---|
| a compound of Table 1 | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| 2.6. Emulsifiable concentrate | |
|---|---|
| a compound of Table 1 | 10% |
| octylphenol polyethlene glycol ether (4–5 moles of ethylene oxide) | 3% |
| calcium dodecylbenzenesulfonate | 3% |
| castor oil polyglycol ether (36 moles of ethylene oxide) | 4% |
| cyclohexanone | 30% |
| xylene mixture | 50% |

Emulsions of any required concentration can be obtained from this concentrate by dilution with water.

| 2.7. Dusts | (a) | (b) |
|---|---|---|
| a compound of Table 1 | 5% | 8% |
| talcum | 95% | — |
| kaolin | — | 92% |

Ready-for-use dusts are obtained by mixing the active ingredient with the carrier, and grinding the mixture in a suitable mill.

| 2.8. Extruder granulate | |
|---|---|
| a compound of Table 1 | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| 2.9. Coated granulate | |
|---|---|
| a compound of Table 1 | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granulates are obtained in this manner.

| 2.10. Suspension concentrate | |
|---|---|
| a compound of Table 1 | 40% |
| ethylene glycol | 10% |
| nonylphenol polyethylene glycol (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

3. Biological Examples

EXAMPLE 3.1.

Action against *Puccinia graminis* on wheat (a) Residual-protective action

Wheat plants are treated 6 days after sowing with a spray mixture (0.02% active ingredient) prepared from a wettable powder formulation of the test compound. After 24 hours the treated plants are infected with a uredospore suspension of the fungus. The infected plants are incubated for 48 hours at 95–100% relative humidity and about 20° C. and then stood in a greenhouse at about 22° C. Evaluation of rust pustule development is made 12 days after infection. (b) Systemic action Wheat plants are treated 5 days after sowing with a spray mixture (0.006% active ingredient, based on the volume of the soil) prepared from a wettable powder formulation of the test compound. After 48 hours the treated plants are infected with a uredospore suspension of the fungus. The plants are then incubated for 48 hours at 95–100% relative humidity and about 20° C. and then stood in a greenhouse at about 22° C. Evaluation or rust pustule development is made 12 days after infection.

Compounds of Table 1 exhibited a good activity against Puccinia fungi. Puccinia attack was 100% on untreated and infected control plants. Compounds 1.2, 1.15, 1.24, 1.30 and 1.32 and others inhibited Puccinia attack to 0 to 5%.

EXAMPLE 3.2

Action against *Cercospora arachidicola* in groundnut plants

Residual protective action

Groundnut plants 10–15 cm in height are sprayed with a spray mixture (0.006% active ingredient) prepared froma wettable powder formulation of the test compound, and infected 48 hours later with a conidia suspension of the fungus. The infected plants are incubated for 72 hours at about 21° C. and high humidity and then stood in a greenhouse until the typical leaf specks occur. Evaluation of the fungicidal action is made 12 days after infection and was based on the number and size of the specks.

Compared with untreated and infected control plants (number and size of the specks=100%), Cercospora attack on groundnut plants treated with compounds of Table 1 was substantially reduced. Thus compounds 1.1, 1.2 and 1.15 inhibited the occurrence of specks almost completely on the above tests.

EXAMPLE 3.3

Action against *Erysiphe graminis* on barley

Residual protective action

Barley plants about 8 cm in height are sprayed with a spray mixture (0.02% active ingredient) prepared from a wettable powder formulation of the test compound. The treated plants are dusted with conidia of the fungus after 3 to 4 hours. The infected barley plants are stood in a greenhouse at about 22° C. The fungus attack is evaluated after 10 days. Compounds of Table 1 were very effective against Erysiphe attack on barley.

EXAMPLE 3.4

Residual-protective action against *Venturia inaequalis* on apple shoots

Apple cuttings with 10–20 cm long fresh shoots are sprayed with a spray mixture (0.06% active ingredient) prepared from a wettable powder formulation of the test compound. The plants are infected 24 hours later with a conidia suspension of the fungus. The plants are then incubated for 5 days at 90–100% relative humidity and stood in a greenhouse for a further 10 days at 20°–24° C. Evaluation of scab infestation is made 1 to 5 days after infection.

Compounds of Table 1 exhibited good activity against Venturia on apple shoots. Compounds 1.1, 1.2, 1.15, 1.24, 1.30 and 1.32 inhibited attack to less than 10%. Venturia attack on untreated and infected shoots was 100%.

EXAMPLE 3.5

Action against *Botrytis cinerea* on beans

Residual protective action

Bean plants about 10 cm in height are sprayed with a spray mixture (0.02% active ingredient) prepared from a wettable powder formulation of the test compound. After 48 hours the treated plants are infected with a conidia suspension of the fungus. The infected plants are incubated for 3 days at 95–100% relative humidity and 21° C. and then evaluated for fungus attack. The compounds of Table 1 inhibited the fungus infection very strongly in many cases. At a concentration of 0.02%, compounds 1.1, 1.2, 1.15, 1.24, 1.30 and 1.32 were fully effective (0 to 5% attack). Fungus attack was 100% on untreated and infected bean plants.

EXAMPLE 3.6

Action against *Botrytis cinerea* on applies

Artificially damaged apples are treated by dropping a spray mixture prepared from a wettable powder formulation of the test compound onto the injury sites. The treated fruit is then inoculated with a spore suspension of *Botrytis cinerea* and incubated for 1 week at high humidity and about 20° C. Evaluation is made by counting the number of injury sites attacked by rot and deducing the fungicidal action of the test compound therefrom. Compounds of Table 1 were very effective against Botrytis attack on applies. Compared with untreated controls (100% attack), compounds 1.1, 1.2, 1.15, 1.24, 1.30, 1.32 and others inhibited fungus attack almost completely.

EXAMPLE 3.7

Action against *Alternaria solani* on tomatoes

After a cultivation period of 3 weeks, tomato plants are sprayed with a spray mixture (0.06% active ingredient) prepared from a wettable powder formulation of the test compound. After 24 hours the tomato plants are treated with a conidia suspension of the fungus. Evaluation of fungicidal action is made on the basis of fungus attack after the plants have been incubated for 8 days at high humidity and a temperature of 18°-22° C. Compounds of Table 1 reduced Alternaria attack substantially; thus compounds 1.1, 1.2, 1.15, 1.24, 1.30 and 1.32 inhibited attack completely (0 to 5%).

EXAMPLE 3.8

Action against *Pyricularia* on rice plants

Residual protective action

After a cultivation period of 2 weeks, rice plants are sprayed with a spray mixture (0.02% active ingredient) prepared from a wettable powder formulation of the test compound. After 48 hours the treated plants are infected with a conidia suspension of the fungus. Evaluation of fungus attack is made after incubation for 5 days at 95-100% relative humidity and 24° C.

Compounds of Table 1 inhibited Pyricularia attack effectively. Thus, for example, compounds 1.1, 1.2, 1.15, 1.24, 1.30 and 1.32 reduced attack to less than 10%.

EXAMPLE 3.9

Action against *Fusarium nivale* in rye

Rye seeds of the Tetrahell variety which are naturally infected with *Fusarium nivale* are dressed on a mixer roll with the test fungicide at a concentration of 60 ppm of active ingredient (based on the weight of the seeds). The infected and treated rye is sown in October in the open with a seeder in plots 3 meters long and in 6 rows. Three replicates are carried out with each test compound. Until evaluation is made, the test plants are cultivated under normal field conditions (preferably in a region with unbroken snow cover during the winter months). To determine the effectiveness of the test compounds, the percentage of plants attacked by Fusarium is assessed in the spring directly after the snow has melted.

Compounds of Table 1 exhibited good activity against Fusarium on rye in this test. On the other hand, Fusarium attack on untreated and infected control plants was 100%.

EXAMPLE 3.10

Action against *Helminthosporium gramineum* on barley

Seeds of winter barley of the "Cl" variety which are naturally infected with *Helminthosporium gramineum* are dressed on a mixer roll with the test fungicide at a concentration of 60 ppm of active ingredient (based on the weight of the seeds). The infected and treated barley is sown in October in the open with a seeder in plots 2 meters long and in 3 rows. Three replicates are carried out with each test compound. Until evaluation is made, the test plants are cultivated under normal field conditions. To determine the effectiveness of the test compounds, the percentage of stalks attacked by Helminthosporium is assessed at the time of ear emergence.

Compounds of Table 1 exhibited good activity against Helminthosporium in this test. On the other hand, Helminthosporium attack on untreated and infected control plants was 100%.

EXAMPLE 3.11

Action against *Tilletia caries* in wheat

Seeds of winter wheat of the Probus variety which are artificially infected with smut spores of *Tilletia caries* (3 g of dry spore material per 1 kg of seeds) are dressed on a mixer roll with the test fungicide at a concentration of 60 ppm of active ingredient (based on the weight of the seeds). The infected and treated wheat is sown in October in the open with a seeder in plots 2 meters long and in 3 rows. Three replicates are carried out with each test compound. To determine the effectiveness of the test compounds, the percentage of ears attacked by Tilletia is assessed at the time of ear ripening.

Compounds of Table 1 exhibited good activity against Tilletia in this test. On the other hand, Tilletia attack on untreated and infected control plants was 100%.

What is claimed is:

1. A compound of formula I

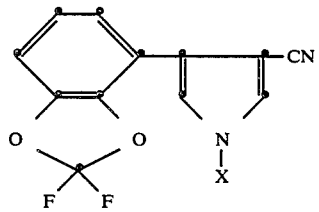

wherein X has the following meanings:

A: hydrogen or $CO-R_1$, wherein $R_1$ is $C_1-C_6$alkyl which is unsubstituted or substituted by halogen or $C_1-C_3$alkoxy; or is $C_3-C_6$alkenyl, $C_3-C_6$alkynyl, or $C_1-C_6$alkoxy which is unsubstituted or substituted by halogen or $C_1-C_3$alkoxy; or is $C_3-C_6$alkenyloxy, or $C_3-C_6$cycloalkyl;

B: $S-R_2$, wherein $R_2$ is $C_1-C_3$haloalkyl;

C: $CH(Y)R_3$, wherein $R_3$ is hydrogen or $C_1-C_8$haloalkyl and Y is hydroxy, halogen or $OC(O)R_4$, wherein $R_4$ is $C_1-C_8$alkyl, $C_1-C_8$haloalkyl, $C_2-C_6$alkenyl, or $C_1-C_6$alkoxycarbonyl; or D: $CH_2-Z$, wherein Z is the group

in which formula each of $R_5$ and $R_6$ independently of the other is hydrogen, $C_1$-$C_6$alkyl which is unsubstituted or substituted by cyano or $C_1$-$C_6$alkoxycarbonyl; or is $C_3$-$C_6$alkenyl, $C_3$-$C_6$alkynyl, $C_3$-$C_7$cycloalkyl, or phenyl which is unsubstituted or substituted by halogen, $C_1$-$C_6$alkyl, $C_1$-$C_6$haloalkyl or $C_1$-$C_6$alkoxy, with the proviso that only $R_5$ or $R_6$ may be hydrogen.

2. A compound of formula I according to claim 1, wherein X is hydrogen or CO—$R_1$, wherein $R_1$ is $C_1$-$C_6$alkyl which is unsubstituted or substituted by halogen or $C_1$-$C_3$alkoxy; or is $C_3$-$C_6$alkenyl, $C_3$-$C_6$alkynyl, or $C_1$-$C_6$alkoxy which is unsubstituted or substituted by halogen or $C_1$-$C_3$alkoxy; or is $C_3$-$C_6$alkenyloxy or, $C_3$-$C_6$cycloalkyl.

3. A compound of formula I according to claim 2, wherein X is hydrogen or CO—$R_1$, wherein $R_1$ is $C_1$-$C_4$alkyl which is unsubstituted or substituted by chlorine, bromine or $C_1$-$C_3$alkoxy; or is $C_3$-$C_4$alkenyl, $C_3$-$C_4$alkynyl, or $C_1$-$C_4$alkoxy which is unsubstituted or substituted by chlorine, bromine or $C_1$-$C_3$alkoxy; or $C_3$-$C_4$alkenyloxy or, $C_3$-$C_6$cycloalkyl.

4. A compound of formula I according to claim 1, selected from the group consisting of
3-(2,2-difluorobenzodioxol-4-yl)-4-cyanopyrrole;
1-acetyl-3-(2,2-difluorobenzodioxol-4-yl)-4-cyanopyrrole;
1-methoxyacetyl-3-(2,2-difluorobenzodioxol-4-yl)-4-cyanopyrrole;
1-methoxycarbonyl-3-(2,2-difluorobenzodioxol-4-yl)-4-cyanopyrrole;
1-allyloxycarbonyl-3-(2,2-difluorobenzodioxol-4-yl)-4-cyanopyrrole;
1-n-propoxyacetyl-3-(2,2-difluorobenzodioxol-4-yl)-4-cyanopyrrole.

5. A microbicidal composition for controlling microorganisms or for protecting living plants from attack by said microorganisms or for preserving perishable storage goods of vegetable or animal origin, which composition contains as active component a microbicidally effective amount of at least one compound as defined in claim 1 and a carrier.

6. A microbicidal composition for controlling microorganisms or for protecting living plants from attack by said microorganisms or for preserving perishable storable goods of vegetable or animal origin, which contains as active component a microbicidally effective amount of at least one compound as defined in claim 4 and a carrier.

7. A composition according to claim 5, which comprises 0.1 to 99% of a compound of formula I, 99.9 to 1% of a solid or liquid adjuvant and 0 to 25% of a surfactant.

8. A composition according to claim 7, which comprises 0.1 to 95% of a compound of formula I, 99.8 to 5% of a solid or liquid adjuvant and 0.1 to 25% of a surfactant.

9. A method of controlling phytopathogenic microorganisms or of protecting cultivated plants from attack by said microorganisms, which method comprises applying to said plants, to parts of plants or to the locus thereof a compound of formula I according to claim 1.

10. A method of dressing seeds and plant cuttings to afford protection against attack by fungus organisms, which method comprises applying to said seeds or plant cuttings a compound of formula I according to claim 1.

11. A method of preserving storable goods of vegetable and/or animal origin or of protecting said goods from attack by harmful microorganisms, which method comprises treating said goods with a microbicidally effective amount of a compound of formula I according to claim 1.

* * * * *